United States Patent
Bernard et al.

(10) Patent No.: US 9,926,587 B2
(45) Date of Patent: Mar. 27, 2018

(54) COSMETIC USE OF CHITINASE-TYPE PROTEINS

(75) Inventors: Dominique Bernard, Paris (FR); Mark Donovan, Berville (FR)

(73) Assignee: L'OREAL, Paris (FR)

(*) Notice: Subject to any disclaimer, the term of this patent is extended or adjusted under 35 U.S.C. 154(b) by 785 days.

(21) Appl. No.: 12/515,161

(22) PCT Filed: Nov. 19, 2007

(86) PCT No.: PCT/FR2007/001896
§ 371 (c)(1),
(2), (4) Date: Aug. 4, 2009

(87) PCT Pub. No.: WO2008/068428
PCT Pub. Date: Jun. 12, 2008

(65) Prior Publication Data
US 2010/0056424 A1    Mar. 4, 2010

Related U.S. Application Data

(60) Provisional application No. 60/874,283, filed on Dec. 12, 2006.

(30) Foreign Application Priority Data

Nov. 20, 2006  (FR) ...................... 06 54986

(51) Int. Cl.
| | |
|---|---|
| *C12Q 1/68* | (2006.01) |
| *C12Q 1/34* | (2006.01) |
| *A61K 8/64* | (2006.01) |
| *A61K 38/47* | (2006.01) |
| *A61Q 7/00* | (2006.01) |
| *A61Q 19/00* | (2006.01) |
| *A61Q 19/08* | (2006.01) |
| *G01N 33/50* | (2006.01) |
| *G01N 33/68* | (2006.01) |
| *C12P 21/02* | (2006.01) |

(52) U.S. Cl.
CPC ............... *C12Q 1/34* (2013.01); *A61K 8/64* (2013.01); *A61K 38/47* (2013.01); *A61Q 7/00* (2013.01); *A61Q 19/00* (2013.01); *A61Q 19/007* (2013.01); *A61Q 19/08* (2013.01); *G01N 33/5082* (2013.01); *G01N 33/6893* (2013.01); *G01N 2333/924* (2013.01); *G01N 2500/04* (2013.01); *G01N 2800/20* (2013.01)

(58) Field of Classification Search
CPC .......... A61K 38/47; A61K 8/64; A61Q 19/00; A61Q 19/007; A61Q 19/08; A61Q 7/00; C12Q 1/34; G01N 2333/924; G01N 2500/04; G01N 2800/20; G01N 33/5082; G01N 33/6893
See application file for complete search history.

(56) References Cited

U.S. PATENT DOCUMENTS

| | | | | |
|---|---|---|---|---|
| 6,060,590 | A * | 5/2000 | Bryant ................ | C07K 14/475 530/350 |
| 6,372,212 | B1* | 4/2002 | Gray ..................... | 424/94.61 |
| 6,399,571 | B1 | 6/2002 | Gray et al. | |
| 6,986,995 | B2* | 1/2006 | Rose et al. .......... | 435/7.1 |
| 2002/0012927 | A1* | 1/2002 | Burmer ................ | A61K 8/64 435/6.1 |
| 2002/0086008 | A1 | 7/2002 | Aerts | |
| 2005/0226884 | A1* | 10/2005 | Price et al. .......... | 424/155.1 |

FOREIGN PATENT DOCUMENTS

| | | | | |
|---|---|---|---|---|
| WO | WO 97/40068 | A1 | 10/1997 | |
| WO | WO 00/34469 | A1 | 6/2000 | |
| WO | WO 01/23430 | A2 | 4/2001 | |
| WO | WO 03/054166 | A2 * | 7/2003 | ......... C12N 2320/34 |
| WO | WO 03/107545 | A2 | 12/2003 | |
| WO | WO 2004/028479 | A2 | 4/2004 | |
| WO | WO 2004/041170 | A2 | 5/2004 | |
| WO | WO 2006/089549 | A1 | 8/2006 | |
| WO | WO 2007/027748 | A2 | 3/2007 | |

OTHER PUBLICATIONS

Wermuth et al, Glossary of Terms Used in Medicinal Chemistry, Pure and Appl. Chem, vol. 70, No. 5, pp. 1129-1143.*
Elias, "Stratum Corneum Defensive Functions: An Integrated View" 125 Journal of Investigative Dermatology 183-200 (2005).*
De Ceuninck et al., "YKL-40 (Cartilage gp-39) Induces Proliferative Events in Cultured Chondrocytes and Synoviocytes and Increases Glycosaminoglycan Synthesis in Chondrocytes" 285(4) Biochemical and Biophysical Research Communications 926-931 (2001).*
Hakala et al, "Human Cartilage gp-39, a Major Secretory Product of Articular Chondrocytes and Synovial Cells, Is a Mammalian Member of a Chitinase Protein Family," *Journal of Biological Chemistry*, vol. 268, No. 34, Dec. 5, 1993, pp. 25803-25810.
Malinda et al., "Gp38k, a Protein Synthesized by Vascular Smooth Muscle Cells, Stimulates Directional Migration of Human Umbilical Vein Endothelial Cells," *Experimental Cell Research*, vol. 250, 1999, pp. 168-173.
De Ceuninck et al., "YKL-40 (Cartilage gp-39) Induces Proliferative Events in Cultured Chondrocytes and Synoviocytes and Increases Glycosaminoglycan Synthesis in Chondrocytes," *Biochemical and Biophysical Research Communication*, vol. 285, 2001, pp. 926-931.
Recklies et al., "The chitinase 3-like protein human cartilage glycoprotein 39 (HC-gp39) stimulates proliferation of human connective-tissue cells and activates both extracellular signal-regulated kinase- and protein kinase B-mediated signaling pathways," *Biochemical Journal*, vol. 365, 2002, pp. 119-126.

(Continued)

*Primary Examiner* — Nancy J Leith
(74) *Attorney, Agent, or Firm* — Oliff PLC

(57) ABSTRACT

The present invention relates to the use, notably cosmetic and/or therapeutic, of the YKL-40 protein belonging to the family of chitinase-type proteins, of polypeptides derived from this protein or analogs thereof of a nucleic acid sequence encoding such a polypeptide or of an agent that modulates the activity or expression of such a polypeptide notably for stimulation of terminal epithelial differentiation.

12 Claims, No Drawings

(56) References Cited

OTHER PUBLICATIONS

Rehli et al., "Transcriptional Regulation of CHI3L1, a Marker Gene for Late Stages of Macrophage Differentiation," *Journal of Biological Chemistry*, vol. 278, No. 45, Nov. 7, 2003, pp. 44058-44067.
Shackelton et al., "Identification of a 38-kDa Heparin-binding Glycoprotein (gp38k) in Differentiating Vascular Smooth Muscle Cells as a Member of a Group of Proteins Associated with Tissue Remodeling," *Journal of Biological Chemistry*, vol. 270, No. 22, Jun. 2, 1995, pp. 13076-13083.

* cited by examiner

COSMETIC USE OF CHITINASE-TYPE PROTEINS

The present invention relates to the use, notably cosmetic and/or therapeutic, of the YKL-40 protein belonging to the family of chitinase-type proteins or of polypeptides derived from this protein or of analogs thereof, of a nucleic acid sequence encoding such a polypeptide or of an agent that modulates the activity or expression of such a polypeptide notably for stimulation of terminal epithelial differentiation.

The epithelia are tissues whose cells are contiguous and tightly packed together and are supported on a basement membrane. They form either an external coating, for example on the surface of the skin, or the epidermis, or an internal coating, on the surface of a mucous membrane. They can also form glands.

The epidermis is an epithelium, conventionally divided into a basal layer of keratinocytes containing, notably, epidermal stem cells and constituting the germinative layer (stratum germinativum) of the epidermis, a spinous layer (stratum spinosum) constituted of several layers of polyhedral cells arranged on the basal layer, a granular layer (stratum granulosum) comprising one to three layers of so-called flattened cells containing distinct cytoplasmic inclusions, the keratohyalin granules, and finally, a number of upper layers, called the cornified layer (stratum corneum) constituted of keratinocytes at the final stage of their differentiation, called corneocytes.

The epithelia are structures whose homeostasis results from the action of a finely controlled ensemble of intracellular and extracellular signals acting in all stages of proliferation, migration, cellular differentiation, as well as the synthesis of the various components of the extracellular matrix.

These signals can, notably, result from the action of factors produced by keratinocytes.

The maintenance of proper physiological functions of an epithelium notably involves terminal epithelial differentiation and/or the synthesis of proteoglycans.

In the case of an epidermis for example, epidermal differentiation follows a process of maturation in which keratinocytes of the basal layer differentiate and migrate, finally forming corneocytes, which are completely keratinized dead cells.

This differentiation is the end result of perfectly coordinated phenomena which lead to the maintenance of a constant thickness and thus ensure homeostasis of the epidermis.

Numerous skin problems or pathologies may result from dysfunction of homeostasis of the epithelium, and notably of terminal epithelial differentiation of the keratinocytes and/or synthesis of proteoglycans.

In the case of an epidermis, these problems may be reflected, for example, in various disorders of aged skin, resulting either from aging of the epidermis due to the passage of time (chronological aging) or aging due to exposure to various external factors, such as exposure to sunlight (photoaging).

They may also be reflected in disorders of the barrier function of the skin against microorganisms, hyperkeratoses, xerosis (or dry skin), ichthyoses, psoriasis, disorders of desquamation, certain benign or malignant tumoral lesions, or disorders of the hair follicles.

However, poor understanding of the detailed physiological mechanisms and of the ensemble of intracellular and extracellular signals involved in homeostasis of the epithelia, the terminal differentiation of the keratinocytes and the synthesis of proteoglycans makes it difficult to prepare cosmetic or therapeutic compositions that can be employed effectively in the treatment of the aforementioned epithelial, and notably cutaneous, disorders.

Thus, there is a need for new compounds allowing specific modulation of the terminal differentiation of the keratinocytes.

There is also a need for new compounds allowing specific modulation of the synthesis of proteoglycans in the epithelia and notably in the epidermis.

There is also a need for new cosmetic and/or therapeutic targets whose modulation can make it possible to regulate the homeostasis of the epithelia and notably of the epidermis.

There is also a need for new compounds that can be used for purposes of reinforcing the skin's defenses.

There is also a need for new compounds that can be used for purposes of preparing cosmetic and/or therapeutic compositions intended for the treatment and/or prophylaxis of the skin disorders mentioned above.

The present invention aims to satisfy these needs.

More specifically, the present invention results from the identification by the inventors, for the first time, of the presence of the YKL-40 polypeptide in the stratum corneum of the epidermis, as well as in the hair follicle.

The YKL-40 polypeptide (YKL referring to the N-terminal sequence of the mature polypeptide SEQ ID NO 5), also known by the name Human Cartilage glycoprotein 39 (HC gp-39), is a polypeptide of 383 amino acids (SEQ ID NO 4; P36222, www.ncbi.nlm.nih.gov), initially isolated from culture of human articular chondrocytes, and whose maturation, by elimination of the signal sequence formed by the first 21 amino acids (SEQ ID NO 6), leads to the extracellular release of the polypeptide identified by the sequence SEQ ID NO 5 (Hakala et al., J. Biol. Chem., 1993, 268:25803).

Apart from its presence in the articular chondrocytes, this protein has also been detected in other tissues or organs such as synoviocytes, neutrophils, macrophages, the synovial fluid of patients with rheumatoid polyarthritis, the liver or the retina. Up to now, however, it had never been detected in the epidermis or the hair follicle.

It is a glycoprotein with an apparent molecular weight varying from 38 to 40 kDa depending on the method of measurement employed.

This protein (or polypeptide) is characterized by the presence of numerous sequence similarities with chitinases of bacterial and/or fungal origin. However, it does not appear to possess chitinolytic activity or glycosidase activity.

Certain physiological functions of the YKL-40 protein are notably discussed in the following documents: MALINDA et al., Exp. Cell Res., 1999, 250:168; DE CEUNINCK et al., Bioehem, Biophys. Res. Commun, 2001, 285:926, RECKLIES et al., Biochem. J., 2002, 365:119, REHLI et al., J. Biol. Chem., 2003, 278:44058; SHACKELTON et al., J. Biol. Chem., 1995, 270:13076.

For its part, application WO 03/107545 proposes compositions for topical application combining the protein HC-gp39 with glycosaminoglycans or with hyaluronic acid, in order to improve the beneficial effect of the latter compounds on skin affected by aging or by injuries, for example of a surgical nature.

As for U.S. Pat. No. 6,060,590, it describes the use of chitinase-type proteins for promoting healing of damaged tissue, and notably of the skin.

Unexpectedly, the inventors have henceforth characterized the expression of the YKL-40 protein by the keratinocytes in various cutaneous zones of an individual, as well as in the hair follicle.

Thus, according to one of its first aspects, the present invention relates to a cosmetic or alternatively nontherapeutic use of an effective amount of at least one polypeptide derived from the YKL-40 protein and, notably, of amino acid sequence encoded by a nucleic acid sequence represented completely or partially by a sequence selected from SEQ ID NO 1, SEQ ID NO 2, SEQ ID NO 3, an analog thereof or a fragment thereof, of at least one nucleic acid sequence encoding such a polypeptide or of at least one agent that modulates the activity or expression of such a polypeptide and/or its release from a proteoglycan matrix of an epithelium as an agent that can be used for stimulation of terminal epithelial differentiation, and notably of the epidermal type, and/or stimulation of epithelial, and notably epidermal, synthesis of proteoglycans.

According to another of its aspects, the present invention also relates to a use of an effective amount of at least one polypeptide derived from the YKL-40 protein and, notably, with amino acid sequence encoded by a nucleic acid sequence represented completely or partially by a sequence selected from SEQ ID NO 1, SEQ ID NO 2, SEQ ID NO 3, an analog thereof or a fragment thereof, of at least one nucleic acid sequence encoding such a polypeptide or of at least one agent that modulates the activity or expression of such a polypeptide and/or its release from a proteoglycan matrix of an epithelium for the preparation of a therapeutic composition intended to stimulate epithelial, and in particular epidermal, terminal differentiation, epithelial, and notably epidermal, synthesis of proteoglycans, epithelial, and notably cutaneous, defenses against microorganisms.

In particular, the compositions considered according to the invention can be intended for stimulation of the terminal differentiation of the keratinocytes.

In particular, the compositions considered according to the invention are free from glycosaminoglycans and/or hyaluronic acid.

In the sense of the present invention, the expression "effective amount" is intended to mean the minimum amount required for observation of the expected effect, namely a cosmetic effect or a therapeutic effect, it being understood that the effective amounts required for obtaining a cosmetic effect or a therapeutic effect may be identical or different, depending on circumstances. In the sense of the invention, "cosmetic use" denotes a use intended mainly to provide an aesthetic effect.

More particularly, "cosmetic composition" is intended to denote, in the sense of the invention, in accordance with European Directive 76768EEC, a composition intended to come in contact with keratinous materials, such as the skin, the mucosae, the nails, the bristle and hair systems, in order to clean them, modify their appearance, and/or protect them and/or keep them in good condition.

In the sense of the invention, "therapeutic composition" denotes a composition intended to provide a prophylactic or curative effect with respect to epithelial, and notably epidermal, disorders, recognized as reflecting a pathologic state.

"Prevention" means, in the sense of the invention, reduction of the risk of occurrence of a phenomenon, for example a pathology.

A composition according to the invention can, in particular, be intended for preventing and/or treating a thinning of an epidermis and/or a loss of firmness, of elasticity, of density and/or of tonicity of an epidermis and/or the signs of aging of the skin, such as wrinkles and lines.

"Cutaneous signs of aging" means any changes of the outward appearance of the skin due to aging whether it be chronobiological and/or photo-induced, for example wrinkles and lines, withered skin, lack of skin elasticity and/or tone, the thinning of the dermis and/or the degradation of collagen fibers leading to the appearance of skin that is soft and wrinkled. We also mean all the internal changes of the skin, which are not always reflected in an altered outward appearance, for example all the internal degradations of the skin, particularly of the fibers of elastin, or elastic fibers, following exposure to ultraviolet radiation.

According to another embodiment, a composition according to the invention can, notably, be intended for preventing and/or treating cutaneous signs of dryness, in particular for preventing and/or treating dehydration of an epidermis.

A composition according to the invention can, in particular, be intended for preventing and/or treating the effects of chronological aging of an epidermis or of the lips or of the scalp.

According to another aspect, the present invention also relates to the use of at least one polypeptide according to the invention as a tool for screening biological or chemical compounds that are able to modulate the expression and/or the biological activity of said polypeptide and/or the release of said polypeptide from a proteoglycan matrix, notably from an epithelium.

In particular, it relates to a method of screening anti-aging actives comprising at least the stages consisting of:

a) contacting at least one polypeptide according to the invention with at least one chemical or biological compound to be tested, in conditions favoring manifestation of the biological activity of said polypeptide, and b) determining the biological activity of said polypeptide.

According to yet another of its aspects, the present invention also relates to the use of at least one biological or chemical compound that is able to modulate the expression and/or the biological activity of said polypeptide and/or the release of a polypeptide according to the invention from a proteoglycan matrix of an epithelium, and notably of an epidermis, for the preparation of a composition intended for promoting healing of said epithelium, and notably of said epidermis.

According to yet another of its aspects, the present invention also relates to the use of at least one polypeptide according to the invention, or of a nucleic acid sequence encoding said polypeptide, as a tool for characterization of a condition of an epithelium, and notably of an epidermis.

Definition of Polypeptide

According to one embodiment, a polypeptide suitable for the invention can have an amino acid sequence represented completely or partially by a sequence selected from SEQ ID NO 4, SEQ ID NO 5, SEQ ID NO 6 or an analog thereof or a fragment thereof.

In the sense of the present invention, unless stated otherwise, YKL-40 is generally intended to denote the proprotein form (SEQ ID NO 4) and the mature form of the polypeptide (SEQ ID NO 5).

"Analog of a polypeptide" denotes any polypeptide displaying a sequence homology, in particular with respect to one of the characteristic sequences of said polypeptide, as well as a biological activity of the same nature.

Said compound can be a peptidomimetic agent.

The homology can be at least 85%, for example at least 90%, and for example at least 95%. The homology can be determined by visual comparison or by means of any information processing tool generally used in this field.

The sequence homology can result from changes following mutation or variation in the sequences of the peptides according to the invention arising either from the deletion of one or more amino acids, or from the insertion of one or more amino acids, or alternatively from the substitution of one or more amino acids in the characteristic sequences of a polypeptide according to the invention.

In the sense of the invention, "polypeptide fragment" is intended to mean any portion of a polypeptide according to the invention comprising at least two, at least three, in particular at least 4 and more particularly at least eight consecutive amino acids of said polypeptide, and an appreciably similar biological activity.

"Characteristic sequence of the polypeptide" means, notably with reference to YKL-40, the proprotein sequence constituted by the sequence SEQ ID NO 4, the sequence of the mature protein identified by SEQ ID NO 5, and the sequence identified by SEQ ID NO 6, constituted of the first 21 N-terminal amino acids eliminated during maturation of the protein.

According to one embodiment, the polypeptides identified by the sequences SEQ ID NO 4 and SEQ ID NO 5, or analogs thereof may be preferred for the application of the present invention.

Generally, the polypeptide analogs can include conservative substitutions relative to the amino acid sequence of the natural polypeptide.

Several of these modifications can be combined.

As examples of mutations that can be considered in the present invention, we may mention, nonexhaustively, the replacement of one or more amino acid residues with amino acid residues having a similar hydropathic index though without substantially affecting the biological properties of the polypeptide, and notably its biological activity such as its activity for stimulating the proliferation and/or migration and/or terminal differentiation of the keratinocytes or for stimulating the synthesis of proteoglycans in an epithelium, and in particular in the epidermis, or for improving the defenses of an epithelium, and notably of the epidermis, against microorganisms.

The hydropathic index is an index ascribed to the amino acids in relation to their hydrophobicity and their charge (Kyte et al. (1982), J. Mol. Biol., 157: 105).

A polypeptide or analog also covered by the present invention can be a polypeptide that has undergone one or more posttranslational modification(s).

The term "posttranslational modification(s)" is intended to encompass all the modifications that a peptide or a protein can undergo following its synthesis in a cell, for example a phosphorylation or phosphorylations, a glycosylation or glycosylations, a lipidation or lipidations, such as a farnesylation or a palmitoylation, a structural rearrangement such as formation of disulfide bridges and/or cleavage within the peptide sequence.

Moreover, the analog displays substantially the same biological activity as the natural polypeptide.

According to one embodiment, a polypeptide suitable for the application of the invention can also be a natural or synthetic polypeptide, obtainable in a particular case after enzymatic or chemical lysis of YKL-40 or by chemical or biological synthesis or by extraction from a biological tissue, for example the skin, expressing this polypeptide naturally or after transduction, as well as the various posttranslational forms thereof, or alternatively any natural or synthetic polypeptide whose sequence comprises totally or partially (completely or partly) an amino acid sequence mentioned above, for example the variants and the analogs.

A person skilled in the art can obtain a polypeptide according to the invention by methods based on recombinant DNA, for example those described in "Molecular Cloning—A Laboratory Manual" (2nd edition), Sambrook et al., 1989, Vol. I-III, Coldspring Harbor Laboratory, Coldspring Harbor Press, NY, (Sambrook).

According to another embodiment, a polypeptide suitable for the application of the invention can also be a polypeptide as defined previously in which at least one residue has been replaced with an amino acid residue of similar hydropathic index, as defined previously.

According to another embodiment, a polypeptide suitable for application of the invention can also be a polypeptide as defined previously fused with another polypeptide, a hydrophilic or hydrophobic targeting agent, a bioconversion precursor, an agent for luminescent, radioactive or calorimetric labeling.

In a nonlimiting manner, we may mention as examples of compounds that can be coupled to a polypeptide according to the invention, fluorescent proteins such as the Green Fluorescent Protein, fluorescent chemical compounds such as rhodamine, fluorescein, or Texas Red, phosphorescent compounds, radioactive elements, such as $^3$H, $^{35}$S, $^{121}$I, or $^{125}$I, or agents for colorimetric labeling such as the chromogenic substrates sensitive to the action of galactosidase, peroxidase, chloramphenicol acetyltransferase, luciferase or alkaline phosphatase.

Depending on the nature of the compounds that can be coupled to a polypeptide according to the invention, coupling can be effected by chemical methods, notably by means of reactive chemical functions or by methods of molecular biology known by a person skilled in the art.

Definition of Nucleic Acid Sequences

According to one embodiment, the present invention also relates to nucleic acid sequences encoding a polypeptide of the invention and their application in the various uses and methods according to the invention.

Thus, the present invention also relates to the use of nucleic acid sequences, notably of deoxyribonucleic acids, or of ribonucleic acids encoding a polypeptide according to the invention, notably the sequences corresponding to at least one nucleic acid sequence encoding SEQ ID NO: 1, SEQ ID NO: 2, SEQ ID NO 3, analogs thereof or a fragment thereof for the preparation of a composition according to the invention.

In the sense of the present invention, "fragment of nucleic acid sequence" means a nucleic acid sequence encoding all or part of a polypeptide according to the invention, or an analog thereof, and in particular a nucleic acid sequence selected from SEQ ID NO 1 (encoding the proprotein form), SEQ ID NO 2 (encoding the protein form), SEQ ID NO 3 (encoding the signal peptide) or an analog thereof.

"Analog of a nucleic acid sequence" means any nucleic acid sequence, optionally resulting from the degeneration of the code of the nucleic acids, and encoding a sequence of a polypeptide identical or analogous to the sequence of the polypeptide encoded by said nucleic acid sequence.

The nucleic acid sequences can be obtained from all possible sources, namely either animal, in particular from mammals and even more particularly human, or vegetable, or from microorganisms (viruses, phages, bacteria among others) or alternatively from fungi, without prejudging whether they are or are not present naturally in said source organism.

In this case the invention also relates to the use of isolated and purified fragments of nucleic acids encoding the polypeptides considered according to the invention.

A nucleic acid sequence according to the invention can be a sense, antisense or interference sequence corresponding to a sequence encoding a polypeptide according to the invention.

Thus, the present invention also relates to the use of nucleic acid sequences, notably of deoxyribonucleic acids, or of ribonucleic acids encoding a polypeptide according to the invention.

The nucleic acid sequences according to the invention can notably be used for preparing corresponding sense or antisense sequences of ribonucleic acids.

The invention also relates to the use of any polynucleotide, sequence of ribonucleic or deoxyribonucleic acids, sense or antisense, notably "small interfering RNA", corresponding at least to the nucleic acid sequence encoding SEQ ID NO: 1, SEQ ID NO: 2, SEQ ID NO 3 or an analog thereof.

Modulating Agent

According to another embodiment, the invention relates to the use of an agent that modulates the expression, activity and/or release of a polypeptide according to the invention. In particular, the invention relates to the use of a modulating agent that activates the activity of a polypeptide of the invention.

In the sense of the invention, "modulate" means, with respect to a given effect, the action of stimulating or inhibiting said effect.

In the sense of the present invention, the expression "modulating agent or chemical or biological compound that is able to modulate biological activity and/or expression" means any compound that can act, directly or indirectly, on at least one polypeptide according to the invention, or a nucleic acid sequence encoding the latter, or on an element of an intracellular or extracellular signaling pathway, or of a metabolic pathway, involving said polypeptide, or on an element involved in the regulation of the transcription and/or translation of a nucleic acid sequence encoding said polypeptide.

"Biological activity" means, notably with respect to YKL-40, the biological activity of the proprotein (SEQ ID NO 4), the biological activity of the mature form of YKL-40 (SEQ ID NO 5), as well as of the signal peptide comprising the 21 N-terminal amino acids (SEQ ID NO 6).

More particularly, the modulating agent can be an activator of the activity of the polypeptides according to the invention.

In the sense of the present invention, the expression "modulating agent" or "chemical or biological compound that is able to modulate the release" means any compound that can act, directly or indirectly, on at least one polypeptide according to the invention, or any element involved directly or indirectly in the distribution of a polypeptide according to the invention within a proteoglycan matrix and/or in a stable association of a polypeptide according to the invention with said matrix.

Thus, application of the present invention notably makes it possible to offer modulating agents capable of mobilizing the stores of YKL-40 present in a proteoglycan matrix.

In particular, the proteoglycan matrix considered by the invention is a matrix of an epithelium, and notably of an epidermis.

The present invention relates to a method of screening biological or chemical compounds or physicochemical factors that are able to modulate a biological activity of a polypeptide according to the invention comprising at least the stages consisting of:

a) contacting at least one polypeptide according to the invention with at least one chemical or biological compound to be tested, and/or subjecting said polypeptide to said physicochemical factor, in conditions favoring the manifestation of said biological activity of said polypeptide, and b) determining said biological activity of said polypeptide.

In such a method, the biological activity of the polypeptide, in particular its activity of epithelial, and notably epidermal terminal differentiation, notably with respect to the keratinocytes, can, for example, be determined by any method known by a person skilled in the art.

For example and in a nonlimiting manner, we may mention methods of cell culture followed by a characterization of differentiation markers, such as keratin 10, filaggrin or of proliferation markers, for example KI 67 and PNCA.

According to one embodiment, the biological activity of a polypeptide according to the invention can be the stimulation of the synthesis of proteoglycans or of their receptors by cells of an epithelium, in particular of an epidermis.

According to one embodiment, the biological activity of the polypeptide can be compared with a reference value.

A reference value can be obtained by measuring the biological activity of the polypeptide in the absence of any biological or chemical compound to be tested.

Assuming that this measurement of reference value is carried out prior to the application of the biological or chemical compound to be tested, the method according to the invention can in addition permit, if necessary, assessment of the potential efficacy of said compound.

This biological activity must not be affected by the presence of said compound or conversely be inhibited or stimulated.

Assuming that a stimulating effect is found, the test compound can be used for example as an anti-aging active.

A method according to the invention can be carried out on a cellular sample, obtained either from a skin biopsy or from cells in culture.

Advantageously, as cellular sample, we may mention the keratinocytes.

Advantageously, a polypeptide employed in a method according to the present invention can be the YKL-40 protein.

The present invention also relates to a method of screening biological or chemical compounds or a physicochemical factor, for example light, which are able to modulate the expression of a polypeptide according to the invention comprising at least the stages consisting of:

a) contacting at least one nucleic acid sequence encoding a polypeptide according to the invention with at least one chemical or biological compound to be tested, and/or subjecting said sequence to said physicochemical factor in conditions favoring the expression of said sequence, and b) determining the expression of said sequence.

The expression of a nucleic acid sequence can be determined, for example, by means of oligonucleotide probes, by any protocol known by a person skilled in the art.

As examples of methods of detection of nucleic acid sequences, we may mention the chain polymerization reaction (PCR), the reverse-transcriptase chain polymerization reaction (RT-PCR or Q-PCR), Northern blot, ribonuclease protection assay, methods with DNA chips, methods with transcriptomic chips, methods with oligonucleotide chips, and methods of hybridization in situ.

As examples of agents suitable for the detection of a nucleic acid sequence, and in particular of mRNA, we may mention a labeled nucleic acid probe that is able to hydridize with said sequence.

Such a nucleic acid probe can easily be obtained by any method known by a person skilled in the art.

Thus, the nucleic acid sequences according to the invention can be used for making sense and/or antisense oligonucleotide primers, which hybridize in conditions of high stringency with the sequence SEQ ID NO: 1, SEQ ID NO: 2, SEQ ID NO: 3 or an analog thereof.

The expression of a nucleic acid sequence according to the invention can be compared with a reference value obtained, for example, by carrying out a method according to the invention in the absence of a test compound.

The present invention also relates to a method of screening biological or chemical compounds, or anti-aging actives, that are able to modulate the release of a polypeptide according to the invention from a proteoglycan matrix comprising at least the stages consisting of:

a) contacting at least one polypeptide according to the invention with at least one chemical or biological compound to be tested, distributed in a proteoglycan matrix in conditions favoring stable association of said polypeptide with said matrix, b) determining a content of said polypeptide outside of said matrix, and c) comparing said content determined in stage b) with a content of said polypeptide determined in the absence of any chemical or biological compound to be tested.

According to one embodiment, the proteoglycans of the matrix can be of the heparan sulfate type and derivatives thereof.

The comparison carried out in stage c) can provide information as to the property of said test compound for modulating the release of a polypeptide according to the invention.

The determination of a content of polypeptide according to the invention can be carried out by means of any method known by a person skilled in the art.

As examples of methods of detection of a polypeptide, we may mention Western blot, Slot blot, Dot blot, ELISA (Enzyme Linked Immuno-Sorbent Assay) of the singleplex or multiplex type, proteomic or glycomic methods, staining of polypeptides in a polyacrylamide gel with a silver-based stain, with Coomassie Blue or with SYPRO, immunofluorescence, UV absorption, immunohistochemical methods in conventional, electron or confocal microscopy, FRET (fluorescence resonance energy transfer), TR-FRET methods (time resolved FRET), FLIM methods (fluorescence lifetime imaging microscopy), FSPIM methods (fluorescence spectral imaging microscopy), FRAP methods (fluorescence recovery after photobleaching), reporter gene techniques, AFM methods (atomic force microscopy), surface plasmon resonance techniques, microcalorimetry methods, flow cytometry methods, biosensor methods, radioimmuno-assay methods (RIA), isoelectric focusing, and enzymatic tests, methods employing peptide chips, sugar chips, antibody chips, methods of mass spectrometry, methods of spectrometry of the SELDI-TOF type (Ciphergen).

A method according to the invention can be carried out on a sample of epithelium, notably of epidermis, obtained from a skin biopsy or from an epithelial, for example epidermal cellular model or from a sample obtained from a surface notably by means of adhesive (stripping) of stratum corneum.

It is understood that all the cosmetic or therapeutic compositions considered according to the invention employ a physiologically acceptable medium.

The compositions according to the invention include nucleic acid and/or peptide sequences according to the present invention as an active agent, i.e. they are applied in a form and at contents such as to enable them to exert, by themselves, the expected cosmetic or therapeutic effect.

In the sense of the present invention, "physiologically acceptable medium" means a medium suitable for the application of a composition on an epithelium or a keratinous material, such as the skin, the scalp, the lips, the mucosae and keratin fibers such as the hair, the nails and the bristles, or if necessary by the oral or parenteral route.

In the sense of the present invention, "therapeutic" denotes a composition that can be used within the scope of a prophylactic and/or curative treatment, or in a method of evaluation of a condition of an epithelium, and notably of the epidermis.

According to another embodiment, a cosmetic or therapeutic composition according to the invention can additionally include at least one cosmetic and/or therapeutic active agent.

According to one embodiment, said active agent is not hyaluronic acid and/or a glycosaminoglycan.

As examples of active agents for use in the present invention, we may mention cosmetic oils, such as silicone oils, vegetable oils of the triglyceride type, hydrocarbon oils such as Parleam oil and esters of fatty acids and of fatty alcohol.

It may also be possible to use actives for improving the condition of the skin, such as hydrating or moisturizing actives or active agents for improving the natural lipid barrier, such as ceramides, cholesterol sulfates and/or fatty acids and mixtures thereof.

It may also be possible to use enzymes having an activity on the skin, such as proteases, lipases, glucosidases, amidases, cerebrosidases and/or melanases and mixtures thereof.

Other examples of active agents suitable for application of the present invention include: analgesic actives, antiyeast actives, antibacterial actives, antiparasitic actives, antifuingal actives, antiviral actives, steroidal antiinflammatory actives, anesthetic actives, antipruritic actives, keratolytic actives, anti-free-radical actives, antiseborrheic actives, antidandruff actives, antiacne actives, actives aiming to prevent aging of the skin and/or improve its condition, antidermatitis actives, anti-irritant actives, immunomodulating actives, actives for the treatment of dry skin, antiperspirant actives, antipsoriatic actives, actives protecting against UV, antihistaminic actives, wound-healing actives, selftanning actives, antioxidants such as green tea or active fractions thereof, glycerol, Laponite, caffeine, aromatic essential oils, colorants, depigmenting actives, liporegulators, softening, refreshing, deodorizing, desensitizing, bleaching, nourishing actives, actives for reducing differentiation and/or proliferation and/or skin pigmentation and mixtures thereof.

In general, any composition of the invention can be applied on the skin (on any cutaneous zone of the body) Or on the mucosae (buccal, jugal, gingival, genital, conjunctival, etc.).

As is well known, a cosmetic composition can also contain additives that are usual in the field of cosmetics, such as hydrophilic or lipophilic gelling agents, hydrophilic or lipophilic additives, preservatives, antioxidants, solvents, perfumes, fillers, filters, odor absorbers and coloring matter.

The amounts of the various constituents of the compositions according to the invention are those conventionally used in the fields in question.

The amount of chemical or biological compound or of polypeptide, of nucleic acid sequence or of modulating agent according to the invention contained in a composition according to the invention, also called "effective amount" depends, of course, on the nature of the compound and on the desired effect and can therefore vary widely.

To give an order of magnitude, a composition can contain a modulating agent according to the invention or a polypeptide in an amount representing from 0.00001% to 50% of the total weight of the composition, in particular in an amount representing from 0.001% to 10% of the total weight of the composition, and more particularly in an amount representing from 0.1% to 1% of the total weight of the composition.

A composition according to the invention can more particularly be intended for the reduction and/or treatment of disorders that may cause deterioration of the condition of an epithelium, and notably of an epidermis.

A condition of an epithelium covered by the present invention can be a condition associated with a dysfunction of epithelial, in particular epidermal, terminal differentiation, notably of the keratinocytes, and/or a defect of proteoglycan synthesis and/or of a deterioration of the epithelial, and notably cutaneous, defenses against microorganisms.

Such a condition may be of chronological origin (i.e. connected with the passage of time, such as aging of the skin) and/or may be indicative of a skin disorder, associated for example with photoaging.

Thus, a composition according to the invention, notably cosmetic, can in particular be intended for preventing and/or treating a thinning of an epidermis and/or a loss of firmness, of elasticity, of density and/or of tonicity of an epidermis and/or the formation of wrinkles and lines.

According to another embodiment, a composition according to the invention, in particular cosmetic, can notably be intended for preventing and/or treating cutaneous signs of dryness, in particular for preventing and/or treating a dehydration of an epidermis.

A composition according to the invention, notably cosmetic, can also be used for the purposes of treatment of the growth or the moderate loss of the hair or of the bristles.

According to yet another embodiment, a composition according to the invention, notably cosmetic, can be intended for activating hair growth, for activating organogenesis of the hair and/or for increasing the survival of the hair follicles.

According to another embodiment, a composition according to the invention, notably cosmetic, can be intended for preventing and/or treating signs of epidermal aging.

A composition according to the present invention, notably therapeutic, can more particularly be intended for the treatment of a skin disorder such as a disorder of the hydration of the skin, such as xerosis, a parakeratosis, a hyperkeratosis, an ichthyosis, a psoriasis, an atopic dermatitis, an eczema, a rosacea, a lichen, a pruritus, a cutaneous pathology having an inflammatory component or resulting from a deterioration of the immune response, a desquamation, a disturbance of melanogenesis or of sebogenesis, an alopecia, hirsutism, a disorder of cicatrization, or a skin disorder involving phenomena of secretion and processes of cellular invasion, notably within the scope of malignant or benign neoplasms.

A composition according to the invention, notably therapeutic can also be used for the purpose of improving the skin's defenses against infection by pathogens, such as bacteria or yeasts, in order to prevent inflammatory reactions following bacterial infections.

According to a variant embodiment, a composition according to the invention, notably therapeutic, can be intended for preventing and/or treating disorders of the barrier function of an epidermis, notably dermis/epidermis, resulting from an infection by microorganisms.

According to another variant embodiment, a composition according to the invention, notably therapeutic, can be intended for preventing and/or treating disorders of an epidermis such as a desquamation, an ichthyosis, a hyperkeratosis.

According to another aspect, the present invention also relates to the use of at least one polypeptide according to the invention or of at least one nucleic acid sequence encoding said polypeptide, as a tool for characterization of a condition of an epithelium, and notably of an epidermis.

According to one embodiment, the present invention relates to a method of characterization of a condition of an epithelium comprising at least the stages consisting of:

a) determining, in a sample of epithelium, a content of a polypeptide according to the invention, or of a nucleic acid sequence encoding said peptide, and b) comparing said content determined in stage a) with a reference value.

According to one embodiment, a method according to the invention can be carried out on a sample of epithelium, and notably of epidermis, taken from an individual.

A method according to the invention can also be carried out on a sample of epithelium, and notably of epidermis, taken from an epithelial, and notably epidermal, cellular model or from a reconstructed isolated skin in order to assess its condition.

A sample of epithelium can be taken by any method known by a person skilled in the art.

A method according to the invention can be carried out in vitro or ex vivo.

A reference value can be, for example, a content of polypeptide or of nucleic acid sequence determined on a sample of epidermis taken from an epithelium, and notably a normal skin, i.e. satisfactory in physiological terms, such as, for example from young skin.

A reference value can be measured in parallel or following the determination of said content of a polypeptide or of a nucleic acid sequence.

Comparing a content determined against a reference value can make it possible to evaluate a deviation relative to this value.

Analysis of the extent and/or nature of this deviation (negative or positive) may provide information on the condition of the epidermis.

Characterization of a condition of an epidermis can be indicative of a possible skin disorder.

According to one embodiment, a method according to the invention can be employed in a method of in vitro or ex vivo diagnosis of a suspected disorder of an epithelium, and notably of the epidermis, in an individual.

For example, a condition of an epithelium to be evaluated can be selected from desquamation, ichthyosis, hyperkeratosis, dryness of an epidermis, aging or photoaging.

A polypeptide suitable for the application of a method according to the invention can be advantageously the YKL-40 protein.

The determination of a content of polypeptide according to the invention or of nucleic acids according to the invention in a sample of epidermis can be carried out by any protocol known by a person skilled in the art.

As methods of detection of a polypeptide, we may mention those mentioned previously.

Thus, we may envisage detection of the presence of a polypeptide according to the invention by means of an antibody, if necessary in a labeled form.

An antibody that can be used as a tool for evaluating a condition of an epidermis can be obtained by any method known by a person skilled in the art, such as described in "Antibodies: A Laboratory Manual", Cold Spring Harbor Laboratory Press, Cold Spring Harbor, N.Y. (1990).

A nucleic acid sequence suitable for the application of a method according to the invention can be advantageously a nucleic acid sequence encoding YKL-40, for example of the mRNA type.

As examples of methods of detection of nucleic acids according to the invention, we may mention the methods mentioned previously.

According to a variant embodiment, the present invention relates to a method of characterization of a condition of an epithelium, and notably of an epidermis comprising at least the stages consisting of:

a) determining a value of the biological activity of a polypeptide according to the invention in a sample of said epithelium, and b) comparing said value determined in stage a) with a reference value.

Advantageously, a biological activity whose value can be determined can be a biological activity as defined previously.

According to another aspect, the present invention relates to a method of cosmetic treatment of a skin disorder comprising at least one stage consisting of applying on at least one part of the skin, of the mucosae and/or of the keratin fibers, at least one cosmetic composition according to the invention.

In the sense of the present invention, "a" or "one" is to be understood, unless stated otherwise, in the sense of "at least one".

The examples given below are presented for purposes of nonlimiting illustration of the invention.

EXAMPLE I

ELISA Analysis of Samples Obtained by Varnish Stripping from Different Cutaneous Zones of an Individual The analyses are performed on varnish strippings carried out on different cutaneous zones of an individual: leg, arm, forehead, palm and back of the hand.

3×3 cm squares of nylon are used.

Acetone powders (AP) are extracted in buffer PBS+0.1% Triton X-100 at a rate of 100 µl/mg of AP in a Potter.

After centrifugation, the supernatants are collected.

The proteins are determined according to Bradford's method with the Bradford reagent from Bio-Rad. Determination of YKL-40 is performed with the Metra YKL40 ELISA kit (Quidel) from 20 µl of each extract.

The tests are performed in duplicate.

Each result is referred to the proportions of proteins.

The presence of YKL40 is easily detected and quantified on all the cutaneous zones analyzed.

EXAMPLE II

Immunohistochemistry

The hair follicle section is 5 µm.

The primary antibody is a rabbit polyclonal antibody obtained from Osteomedical [Ref 4815] and used at 1:25.

The secondary antibody is a rabbit anti-Ig antibody developed in the goat and coupled to biotin, obtained from Dako and used at 1:500.

Finally, amplification with streptavidin and detection with 3-amino-9-ethyl carbazole (AEC) were performed.

A high concentration of YKL-40 protein is observed at the base of the follicle.

---

The invention claimed is:

1. A method for characterization of a condition of an epidermis, said condition being selected from the group consisting of aging and photoaging, comprising:
   a) determining a content, in a sample of epidermis obtained by stripping and/or in an isolated sample of stratum corneum, of at least one polypeptide encoded by a nucleic acid sequence selected from the group consisting of SEQ ID NO 1, SEQ ID NO 2, and SEQ ID NO 3, or of at least one nucleic acid sequence selected from the group consisting of SEQ ID NO 1, SEQ ID NO 2, and SEQ ID NO 3;
   b) evaluating from the content determined in step a) a deviation relative to a reference value from a reference normal skin satisfactory in physiological terms; and
   c) analyzing said deviation so as to yield information on said condition of the epidermis;
   wherein a positive deviation relative to said reference value is indicative of a condition of aging or photoaging of said epidermis.

2. The method as claimed in claim 1, wherein said polypeptide has an amino acid sequence consisting of SEQ ID NO 4, SEQ ID NO 5, or SEQ ID NO 6.

3. The method as claimed in claim 1, wherein a content of said polypeptide is determined by a method selected from the group consisting of Western blot, Dot blot, ELISA, immunofluorescence, immunohistochemistry, electron microscopy, confocal microscopy, FRET, TR-FRET, FLIM, FSPIM, FRAP, reporter gene techniques, AFM, surface plasmon resonance, micro-calorimetry, flow cytometry, biosensor methods, radioimmuno-assay methods, isoelectric focusing, SELDI-TOF, and Bradford method.

4. The method as claimed in claim 1, wherein a content of said nucleic acid sequence is determined by a method selected from the group consisting of PCR, RT-PCR, Q-PCR, Northern blot, ribonuclease protection assay, and hybridization in situ.

5. The method as claimed in claim 1, wherein said epidermis is from a hair follicle.

6. The method according to claim 1, wherein a content of said polypeptide is detected in step a) by an antibody.

7. The method according to claim 6, wherein said nucleic acid sequence consisting of SEQ ID NO 2.

8. The method according to claim 1, wherein a content of said polypeptide is determined in step a) by ELISA.

9. The method according to claim 1, wherein said nucleic acid sequence consists of SEQ ID NO 2.

10. A method for determining a content of YKL-40 in an epidermis, comprising:
    a) providing a sample of epidermis obtained by stripping and/or an isolated sample of stratum corneum; and
    b) determining a content in said sample of at least one polypeptide encoded by a nucleic acid sequence selected from the group consisting of SEQ ID NO 1, SEQ ID NO 2, and SEQ ID NO 3, or of at least one nucleic acid sequence selected from the group consisting of SEQ ID NO 1, SEQ ID NO 2, and SEQ ID NO 3.

11. A method for characterization of a condition of an epidermis, said condition being selected from the group consisting of aging and photoaging, comprising:
    a) determining a content, in a sample of epidermis obtained by stripping and/or in an isolated sample of stratum corneum, of at least one polypeptide encoded by a nucleic acid sequence selected from the group consisting of SEQ ID NO 1, SEQ ID NO 2, and SEQ ID NO 3, or of at least one nucleic acid sequence encoding a YKL-40 polypeptide;
    b) evaluating from the content determined in step a) a deviation relative to a reference value from a reference normal skin satisfactory in physiological terms; and
    c) analyzing said deviation so as to yield information on said condition of the epidermis;
    wherein a positive deviation relative to said reference value is indicative of a condition of aging or photoaging of said epidermis.

12. A method for determining a content of YKL-40 in an epidermis, comprising:
    a) providing a sample of epidermis obtained by stripping and/or an isolated sample of stratum corneum; and
    b) determining a content in said sample of at least one polypeptide encoded by a nucleic acid sequence selected from the group consisting of SEQ ID NO 1, SEQ ID NO 2, and SEQ ID NO 3, or of at least one nucleic acid sequence encoding a YKL-40 polypeptide.

* * * * *

SEQUENCE LISTING

<160> NUMBER OF SEQ ID NOS: 6

<210> SEQ ID NO 1
<211> LENGTH: 1152
<212> TYPE: DNA
<213> ORGANISM: Homo Sapiens

<400> SEQUENCE: 1

```
atgggtgtga aggcgtctca aacaggcttt gtggtcctgg tgctgctcca gtgctgctct      60
gcatacaaac tggtctgcta ctacaccagc tggtcccagt accgggaagg cgatgggagc     120
tgcttcccag atgcccttga ccgcttcctc tgtacccaca tcatctacag ctttgccaat     180
ataagcaacg atcacatcga cacctgggag tggaatgatg tgacgctcta cggcatgctc     240
aacacactca agaacaggaa ccccaacctg aagactctct tgtctgtcgg aggatggaac     300
tttgggtctc aaagattttc caagatagcc tccaacaccc agagtcgccg gactttcatc     360
aagtcagtac cgccattcct gcgcacccat ggctttgatg ggctggacct tgcctggctc     420
taccctggac ggagagacaa acagcatttt accaccctaa tcaaggaaat gaaggccgaa     480
tttataaagg aagcccagcc agggaaaaag cagtcctgc tcagcgcagc actgtctgcg     540
gggaaggtca ccattgacag cagctatgac attgccaaga tatcccaaca cctgatttc     600 attagcatca tgacctacga ttttcatgga gcctggcgtg gaccacagg ccatcacagt     660
```

```
cccctgttcc gaggtcagga ggatgcaagt cctgacagat tcagcaacac tgactatgct      720
gtggggtaca tgttgaggct gggggctcct gccagtaagc tggtgatggg catccccacc      780
ttcgggagga gcttcactct ggcttcttct gagactggtg ttggagcccc aatctcagga      840
ccgggaattc caggccggtt caccaaggag gcagggaccc ttgcctacta tgagatctgt      900
gacttcctcc gcggagccac agtccataga accctcggcc agcaggtccc ctatgccacc      960
aagggcaacc agtgggtagg atacgacgac caggaaagcg tcaaaagcaa ggtgcagtac     1020
ctgaaggata ggcagctggc aggcgccatg gtatgggccc tggacctgga tgacttccag     1080
ggctccttct gcggccagga tctgcgcttc cctctcacca atgccatcaa ggatgcactc     1140
gctgcaacgt ag                                                         1152

<210> SEQ ID NO 2
<211> LENGTH: 1089
<212> TYPE: DNA
<213> ORGANISM: Homo Sapiens

<400> SEQUENCE: 2
tacaaactgg tctgctacta caccagctgg tcccagtacc gggaaggcga tgggagctgc       60
ttcccagatg cccttgaccg cttcctctgt acccacatca tctacagctt tgccaatata      120
agcaacgatc acatcgacac ctgggagtgg aatgatgtga cgctctacgg catgctcaac      180
acactcaaga acaggaaccc caacctgaag actctcttgt ctgtcggagg atggaacttt      240
gggtctcaaa gattttccaa gatagcctcc aacacccaga gtcgccggac tttcatcaag      300
tcagtaccgc cattcctgcg cacccatggc tttgatgggc tggaccttgc ctggctctac      360
cctggacgga gagacaaaca gcattttacc accctaatca aggaaatgaa ggccgaattt      420
ataaaggaag cccagccagg gaaaaagcag ctcctgctca gcgcagcact gtctgcgggg      480
aaggtcacca ttgacagcag ctatgacatt gccaagatat cccaacacct ggatttcatt      540
agcatcatga cctacgattt tcatggagcc tggcgtggga ccacaggcca tcacagtccc      600
ctgttccgag gtcaggagga tgcaagtcct gacagattca gcaacactga ctatgctgtg      660
gggtacatgt tgaggctggg gctcctgcca gtaagctggt gatgggcat ccccaccttc      720 gggaggagct tcactctggc ttcttctgag actggtgttg gagccccaat ctcaggaccg      780
ggaattccag gccggttcac caaggaggca gggaccttg cctactatga gatctgtgac      840
ttcctccgcg gagccacagt ccatagaacc ctcggccagc aggtcccta tgccaccaag      900 ggcaaccagt gggtaggata cgacgaccag gaaagcgtca aaagcaaggt gcagtacctg      960
aaggataggc agctggcagg cgccatggta tgggccctgg acctggatga cttccagggc     1020
tccttctgcg gccaggatct gcgcttccct ctcaccaatg ccatcaagga tgcactcgct     1080
gcaacgtag                                                            1089

<210> SEQ ID NO 3
<211> LENGTH: 63
<212> TYPE: DNA
<213> ORGANISM: Homo Sapiens

<400> SEQUENCE: 3
atgggtgtga aggcgtctca aacaggcttt gtggtcctgg tgctgctcca gtgctgctct       60
gca                                                                    63

<210> SEQ ID NO 4
<211> LENGTH: 383
```

```
<212> TYPE: PRT
<213> ORGANISM: Homo Sapiens

<400> SEQUENCE: 4

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

<210> SEQ ID NO 5
```

```
<211> LENGTH: 362
<212> TYPE: PRT
<213> ORGANISM: Homo Sapiens

<400> SEQUENCE: 5

Tyr Lys Leu Val Cys Tyr Tyr Thr Ser Trp Ser Gln Tyr Arg Glu Gly
1               5                   10                  15

Asp Gly Ser Cys Phe Pro Asp Ala Leu Asp Arg Phe Leu Cys Thr His
            20                  25                  30

Ile Ile Tyr Ser Phe Ala Asn Ile Ser Asn Asp His Ile Asp Thr Trp
        35                  40                  45

Glu Trp Asn Asp Val Thr Leu Tyr Gly Met Leu Asn Thr Leu Lys Asn
50                  55                  60

Arg Asn Pro Asn Leu Lys Thr Leu Leu Ser Val Gly Gly Trp Asn Phe
65                  70                  75                  80

Gly Ser Gln Arg Phe Ser Lys Ile Ala Ser Asn Thr Gln Ser Arg Arg
                85                  90                  95

Thr Phe Ile Lys Ser Val Pro Pro Phe Leu Arg Thr His Gly Phe Asp
            100                 105                 110

Gly Leu Asp Leu Ala Trp Leu Tyr Pro Gly Arg Arg Asp Lys Gln His
        115                 120                 125

Phe Thr Thr Leu Ile Lys Glu Met Lys Ala Glu Phe Ile Lys Glu Ala
130                 135                 140

Gln Pro Gly Lys Lys Gln Leu Leu Leu Ser Ala Ala Leu Ser Ala Gly
145                 150                 155                 160

Lys Val Thr Ile Asp Ser Ser Tyr Asp Ile Ala Lys Ile Ser Gln His
                165                 170                 175

Leu Asp Phe Ile Ser Ile Met Thr Tyr Asp Phe His Gly Ala Trp Arg
            180                 185                 190

Gly Thr Thr Gly His His Ser Pro Leu Phe Arg Gly Gln Glu Asp Ala
        195                 200                 205

Ser Pro Asp Arg Phe Ser Asn Thr Asp Tyr Ala Val Gly Tyr Met Leu
210                 215                 220

Arg Leu Gly Ala Pro Ala Ser Lys Leu Val Met Gly Ile Pro Thr Phe
225                 230                 235                 240

Gly Arg Ser Phe Thr Leu Ala Ser Ser Glu Thr Gly Val Gly Ala Pro
                245                 250                 255

Ile Ser Gly Pro Gly Ile Pro Gly Arg Phe Thr Lys Glu Ala Gly Thr
            260                 265                 270

Leu Ala Tyr Tyr Glu Ile Cys Asp Phe Leu Arg Gly Ala Thr Val His
        275                 280                 285

Arg Thr Leu Gly Gln Gln Val Pro Tyr Ala Thr Lys Gly Asn Gln Trp
290                 295                 300

Val Gly Tyr Asp Asp Gln Glu Ser Val Lys Ser Lys Val Gln Tyr Leu
305                 310                 315                 320

Lys Asp Arg Gln Leu Ala Gly Ala Met Val Trp Ala Leu Asp Leu Asp
                325                 330                 335

Asp Phe Gln Gly Ser Phe Cys Gly Gln Asp Leu Arg Phe Pro Leu Thr
            340                 345                 350

Asn Ala Ile Lys Asp Ala Leu Ala Thr
        355                 360

<210> SEQ ID NO 6
<211> LENGTH: 21
<212> TYPE: PRT
```

-continued

```
<213> ORGANISM: Homo Sapiens

<400> SEQUENCE: 6

Met Gly Val Lys Ala Ser Gln Thr Gly Phe Val Val Leu Val Leu Leu
1               5                   10                  15

Gln Cys Cys Ser Ala
            20
```